United States Patent
Nagao et al.

(10) Patent No.: US 8,962,155 B2
(45) Date of Patent: Feb. 24, 2015

(54) LIGHT EMITTING DEVICE BASED ON A PYRROMETHENE COMPOUND

(75) Inventors: Kazumasa Nagao, Otsu (JP); Tsuyoshi Tominaga, Otsu (JP)

(73) Assignee: Toray Industries, Inc., Tokyo (JP)

( * ) Notice: Subject to any disclaimer, the term of this patent is extended or adjusted under 35 U.S.C. 154(b) by 355 days.

(21) Appl. No.: 12/740,821

(22) PCT Filed: Oct. 28, 2008

(86) PCT No.: PCT/JP2008/069485
§ 371 (c)(1),
(2), (4) Date: Apr. 30, 2010

(87) PCT Pub. No.: WO2009/057567
PCT Pub. Date: May 7, 2009

(65) Prior Publication Data
US 2010/0264406 A1     Oct. 21, 2010

(30) Foreign Application Priority Data

Nov. 2, 2007   (JP) .................. 2007-285862

(51) Int. Cl.
| | | |
|---|---|---|
| *H01L 51/54* | (2006.01) | |
| *C09K 11/06* | (2006.01) | |
| *C07F 5/02* | (2006.01) | |
| *C07D 207/44* | (2006.01) | |
| *C07D 235/18* | (2006.01) | |
| *C07D 307/80* | (2006.01) | |
| *C07D 471/04* | (2006.01) | |
| *H01L 51/00* | (2006.01) | |
| *H05B 33/14* | (2006.01) | |
| *H01L 51/50* | (2006.01) | |

(52) U.S. Cl.
CPC .............. *C07F 5/022* (2013.01); *C07D 207/44* (2013.01); *C07D 235/18* (2013.01); *C07D 307/80* (2013.01); *C07D 471/04* (2013.01); *C09K 11/06* (2013.01); *H01L 51/008* (2013.01); *H05B 33/14* (2013.01); *C09K 2211/1096* (2013.01); *H01L 51/0054* (2013.01); *H01L 51/006* (2013.01); *H01L 51/0072* (2013.01); *H01L 51/0073* (2013.01); *H01L 51/5012* (2013.01); *H01L 51/5048* (2013.01); *Y10S 428/917* (2013.01)
USPC ........... 428/690; 428/917; 313/504; 313/506; 257/40; 257/E51.041; 548/405

(58) Field of Classification Search
None
See application file for complete search history.

(56) References Cited

U.S. PATENT DOCUMENTS

| | | | |
|---|---|---|---|
| 2003/0027016 A1* | 2/2003 | Ara et al. ........... | 428/690 |
| 2003/0082406 A1* | 5/2003 | Murase et al. ............ | 428/690 |
| 2008/0254319 A1* | 10/2008 | Hosokawa et al. ......... | 428/704 |

FOREIGN PATENT DOCUMENTS

| | | |
|---|---|---|
| CN | 101205416 | 6/2008 |
| EP | 1253151 | 10/2002 |
| JP | 2000-208265 A | 7/2000 |
| JP | 2003-012676 A | 1/2003 |
| JP | 2003-151773 A | 5/2003 |
| JP | 2004-107263 A | 4/2004 |
| JP | 2004-200162 A | 7/2004 |
| JP | 2005-053900 A | 3/2005 |
| JP | 200553900 | 3/2005 |
| JP | 2006-245172 A | 9/2006 |
| WO | WO2004/026870 A1 | 4/2004 |

OTHER PUBLICATIONS

Machine translation of JP2006-245172. Date of publication: Sep. 14, 2006.*
European Communication dated Jul. 20, 2011, with Supplemental Search Report for EP08844375 dated Jul. 14, 2011.
International Search Report dated Dec. 22, 2008, application No. PCT/JP2008/069485.
Applied Physics Letters (U.S.), American Institute of Physics, Sep. 21, 1987, vol. 51, No. 12, pp. 913-915.

* cited by examiner

*Primary Examiner* — Andrew K Bohaty
(74) *Attorney, Agent, or Firm* — RatnerPrestia

(57) ABSTRACT

A light emitting device material containing a pyrromethene compound represented by the general formula (1). It realized a luminescent element having a high luminescent efficiency and exellent color purity. Also provided is a luminescent element employing the materials.

13 Claims, No Drawings

LIGHT EMITTING DEVICE BASED ON A PYRROMETHENE COMPOUND

This application is a U.S. National Phase Application of PCT International Application No. PCT/JP2008/069485, filed Oct. 28, 2008, which claims priority to Japanese Patent Application No. 2007-285862, filed Nov. 2, 2007, the contents of these applications being incorporated by reference herein in their entirety.

BACKGROUND OF THE INVENTION

1. Field of the Invention

The present invention provides a light emitting device material useful as a fluorescent dye and a light emitting device using the same, which can be used for display elements, flat panel displays, backlights, lighting, interiors, signs, signboards, electronic cameras, light signal generators, and the like.

2. Background of the Invention

There has recently been considerable research on organic thin-film light emitting devices which emit light when electrons injected from a cathode and holes injected from an anode recombine within an organic luminous body interposed between the cathode and the anode. This light emitting device has been attracting attention because of such a feature that it is thin and capable of emitting high-luminance light under a low driving voltage and emitting multicolor light through selection of an emissive material.

Since C. W. Tang et al. of Eastman Kodak Company showed that an organic thin-film light emitting device emits light at a high luminance, many research institutes have studied this technique. The typical structure of an organic thin-film light emitting device proposed by a research group of Eastman Kodak Company is such that a hole-transporting diamine compound, an emissive layer made of tris(8-quinolinolato)aluminum(III), and a cathode made of a Mg:Ag alloy are formed sequentially on an ITO glass substrate, and the device is able to emit green light of 1,000 cd/m$^2$ at a driving voltage of about 10 V (see Applied Physics Letters, USA, 1987, Vol. 51, No. 12, pp. 913-915).

Moreover, it has intensively been studied to apply the organic thin-film light emitting device as a display or the like since various luminescent colors can be obtained by using various fluorescent materials in the emissive layer. Of emissive materials of the three primary colors, research on green emissive materials is at the most advanced stage and intensive study is being performed so as to improve characteristics of red emissive materials and blue emissive materials.

One of the greatest objects with organic thin-film light emitting devices is to obtain luminance efficiency and color purity of a device at satisfactory levels simultaneously. With regard to a red light emitting device, there are few red emissive materials capable of providing a device that is high in luminance efficiency and excellent in color purity. For example, a pyrromethene compound, which is a compound that exhibits high luminance light emission, is known as a red dopant material (see Japanese Unexamined Patent Publication No. 2000-208265). It is also known that introduction of an aromatic ring or the like into a pyrromethene skeleton produces red light emission (see Japanese Unexamined Patent Publication No. 2003-12676). Moreover, a technique of the use for a red light emitting device of a thermally stable pyrromethene derivative with which a margin of a decomposition temperature and a sublimation temperature has been secured has been disclosed (see Japanese Unexamined Patent Publication No. 2005-53900). However, none of them achieves both luminance efficiency and color purity sufficiently.

SUMMARY OF THE INVENTION

Thus, the present invention provides a light emitting device material which makes it possible to produce a light emitting device being high in luminance efficiency and excellent in color purity, and a light emitting device including the same.

The present invention according to one aspect provides a light emitting device material containing a pyrromethene compound represented by the following formula (1).

[Formula 1]

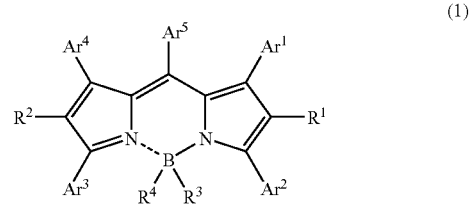

(1)

In the formula (1), $R^1$ to $R^4$ each may be the same or different and are selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an aryl thioether group, an aryl group, a heteroaryl group, halogen, a cyano group, an amino group, a silyl group, and a ring structure formed between adjacent substituents. $Ar^1$ to $Ar^5$ each represent an aryl group, provided that $Ar^1 \neq Ar^2$ or $Ar^3 \neq Ar^4$, wherein $\neq$ means that the groups are different in structure.

Moreover, the present invention is directed to a light emitting device including at least an anode, a cathode, and an emissive layer, the emissive layer being located between the anode and the cathode and being capable of emitting light through application of electric energy, wherein the emissive layer contains a pyrromethene compound represented by the formula (1).

The light emitting device material according to one aspect of the present invention can provide a light emitting device material that can be used for a light emitting device and so on and is high in light emitting performance. According to an embodiment of the present invention, a light emitting device that is high in luminance efficiency and excellent in color purity is obtained.

DETAILED DESCRIPTION OF THE INVENTION

The pyrromethene compound represented by the formula (1) to be used in embodiments of the present invention is explained.

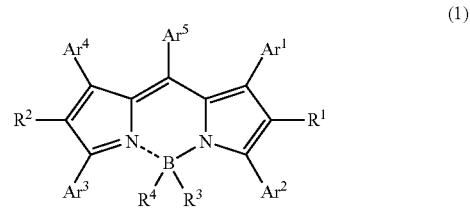

(1)

$R^1$ to $R^4$ each may be the same or different and are selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an aryl thioether group, an aryl group, a heteroaryl group, halogen, a cyano group, an amino group, a silyl group, and a ring structure formed between adjacent substituents. $Ar^1$ to $Ar^5$ each represent an aryl group, provided that $Ar^1 \neq Ar^2$ or $Ar^3 \neq Ar^4$, wherein $\neq$ means that the groups are different in structure.

Among these substituents, the alkyl group represents a saturated aliphatic hydrocarbon group, such as a methyl group, an ethyl group, an n-propyl group, an isopropyl group, an n-butyl group, a sec-butyl group, or a tert-butyl group, and it may or may not have a substituent. When the alkyl group is substituted, the additional substituent is not particularly limited and examples thereof includes an alkyl group, an aryl group, and a heteroaryl group, and this respect is common to the following description. Although the number of carbon atoms of the alkyl group is not particularly limited, it is usually in the range of 1 or more and 20 or less, more preferably in the range of 1 or more and 8 or less, and the alkyl group is even more preferably a methyl group or a tert-butyl group.

The cycloalkyl group represents a saturated alicyclic hydrocarbon group, such as a cyclopropyl group, a cyclohexyl group, a norbornyl group, or an adamantyl group, and it may or may not have a substituent. Although the number of carbon atoms of an alkyl group portion is not particularly limited, it is usually in the range of 3 or more and 20 or less.

The heterocyclic group represents an aliphatic ring having an atom other than carbon in the ring, such as a pyran ring, a piperidine ring, or a cyclic amide, and it may or may not have a substituent. Although the number of carbon atoms of the heterocyclic group is not particularly limited, it is usually in the range of 2 or more and 20 or less.

The alkenyl group represents an unsaturated aliphatic hydrocarbon group containing a double bond, such as a vinyl group, an allyl group, or a butadienyl group, and it may or may not have a substituent. Although the number of carbon atoms of the alkenyl group is not particularly limited, it is usually in the range of 2 or more and 20 or less.

The cycloalkenyl group represents an unsaturated alicyclic hydrocarbon group containing a double bond, such as a cyclopentenyl group, a cyclopentadienyl group, or a cyclohexenyl group, and it may or may not have a substituent.

The alkynyl group represents an unsaturated aliphatic hydrocarbon group containing a triple bond, such as an ethynyl group, and it may or may not have a substituent. Although the number of carbon atoms of the alkynyl group is not particularly limited, it is usually in the range of 2 or more and 20 or less.

The alkoxy group represents a functional group to which an aliphatic hydrocarbon group has been attached via an ether bond, such as a methoxy group, an ethoxy group, or a propoxy group, and the aliphatic hydrocarbon group may or may not have a substituent. Although the number of carbon atoms of the alkoxy group is not particularly limited, it is usually in the range of 1 or more and 20 or less, more preferably in the range of 1 or more and 8 or less, and the alkoxy group is even more preferably a methoxy group. The methoxy group may be located at any of the para position, the meta position, or the ortho position of the aryl group.

The alkylthio group is a group resulting from replacement of an oxygen atom of the ether bond of an alkoxy group by a sulfur atom. The hydrocarbon group in the alkylthio group may or may not have a substituent. Although the number of carbon atoms of the alkylthio group is not particularly limited, it is usually in the range of 1 or more and 20 or less.

The arylether group represents a functional group to which an aromatic hydrocarbon group has been attached via an ether bond, such as a phenoxy group, and the aromatic hydrocarbon group may or may not have a substituent. Although the number of carbon atoms of the arylether group is not particularly limited, it is usually in the range of 6 or more and 40 or less.

The aryl thioether group is a group resulting from replacement of an oxygen atom of the ether bond of an arylether group by a sulfur atom. The aromatic hydrocarbon group in the arylether group may or may not have a substituent. Although the number of carbon atoms of the arylether group is not particularly limited, it is usually in the range of 6 or more and 40 or less.

The aryl group represents an aromatic hydrocarbon group, such as a phenyl group, a naphthyl group, a biphenyl group, an anthracenyl group, a phenanthryl group, a terphenyl group, or a pyrenyl group. The aryl group may be either unsubstituted or substituted. Although the number of carbon atoms of the aryl group is not particularly limited, it is usually in the range of 6 or more and 40 or less.

The heteroaryl group represents a cyclic aromatic group having one atom (or two) or more atoms other than carbon in the ring, such as a furanyl group, a thiophenyl group, a pyrrolyl group, a benzofuranyl group, a benzothiophenyl group, an indolyl group, a pyridyl group, or a quinolinyl group, and it may or may not have a substituent. Although the number of carbon atoms of the heteroaryl group is not particularly limited, it is usually preferably in the range of 2 or more and 30 or less. The halogen represents fluorine, chlorine, bromine, or iodine. The cyano group and the amino group may or may not have a substituent. Examples of the substituent include the aforementioned alkyl groups, cycloalkyl groups, aryl groups, and heteroaryl groups.

The silyl group represents a functional group having a bond to a silicon atom, such as a trimethylsilyl group, and it may or may not have a substituent. Although the number of carbon atoms of the silyl group is not particularly limited, it is usually preferably in the range of 3 or more and 20 or less. Usually, the number of silicon atoms is preferably in the range of 1 or more and 6 or less.

Any adjacent two substituents (for example, $R^1$ and $Ar^2$ in the formula (1)) may be combined with each other to form a conjugated or non-conjugated fused ring. The constituent element of the fused ring may include, in addition to carbon, elements selected from nitrogen, oxygen, sulfur, phosphorus, and silicon. The fused ring may further be fused with another ring. In view of the ease with which raw materials are obtained or the synthesis is performed, it is desirable that both $R^3$ and $R^4$ in the formula (1) be fluorine.

$Ar^1$ to $Ar^5$ may each represent an aryl group. Examples of the aryl group are the same as those provided in the foregoing explanation. It is noted that $Ar^1$ $Ar^2$ or $Ar^3 \neq Ar^4$, wherein means that the groups are different in structure. That $Ar^1 \neq Ar^2$ or $Ar^3 \neq Ar^4$ is, in other words, that not "$Ar^1 = Ar^2$ and $Ar^3 = Ar^4$". That is, it means that among all combinations of $Ar^1$ to $Ar^4$, (1) a combination in which $Ar^1 = Ar^2 = Ar^3 = Ar^4$ and (2) a combination in which $Ar^1 = Ar^2$ and $Ar^3 = Ar^4$ but $Ar^1 \neq Ar^3$ are excluded. When $Ar^1 \neq Ar^2$ or $Ar^3 \neq Ar^4$, dispersibility in a thin film increases, so that light emission with high efficiency is obtained.

An aryl group affects, depending upon the kind thereof, various characteristics and properties, such as luminance efficiency, color purity, and heat resistance, of a pyrromethene compound represented by the formula (1). Although some aryl groups improve more than one properties, no aryl group exhibits sufficient performance with respect to all properties. In particular, simultaneous achievement of high luminance efficiency and high color purity is difficult. Therefore, if two or more kinds of aryl groups can be introduced into a pyrromethene compound represented by the formula (1), a compound having luminance characteristics, color purity, and so on with good balance is expected to be obtained.

A pyrromethene compound in which $Ar^1=Ar^2=Ar^3=Ar^4$ can have only one kind of aryl groups. In a pyrromethene compound in which $Ar^1=Ar^2$, $Ar^3=Ar^4$ and $Ar^1 \neq Ar^3$, aryl groups having specific properties are located unevenly on one pyrrole ring. In this case, as described later with regard to the relationship between efficiency and color purity, it is difficult to draw out properties of the respective aryl groups to the utmost.

In contrast to this, since the pyrromethene compound in an embodiment of the present invention makes it possible to locate substituents having certain properties on the left and right pyrrole rings with good balance, it becomes possible to exhibit the properties to the utmost in comparison to the case where the substituents are located unevenly on one pyrrole ring.

This effect is particularly excellent in improving luminance efficiency and color purity with good balance. As for aryl groups which affect color purity, it is desirable that both the pyrrole rings each have one or more such aryl groups because the conjugated system is extended, so that light emission with high color purity is obtained. However, as to a pyrromethene compound in which $Ar^1=Ar^2$ and $Ar^3=Ar^4$ but $Ar^1 \neq Ar^3$, when, for example, an aryl group that affects color purity is introduced into one pyrrole ring and an aryl group that affects efficiency is introduced into the other pyrrole ring, aryl groups that affect color purity are located unevenly on one pyrrole ring, so that the conjugated system does not extend sufficiently and hence color purity is not increased sufficiently. If an aryl group that likewise affects efficiency but has a different structure is introduced into the other pyrrole ring, it is impossible to increase efficiency.

In contrast to this, the pyrromethene compound in an embodiment of the present invention is preferable because one or more aryl groups that affect color purity can be introduced into each of the pyrrole rings and aryl groups that affect efficiency can be introduced into other positions, and therefore both properties can be improved to the utmost. A case where aryl groups that affect color purity are introduced into the positions of $Ar^2$ and $Ar^3$ is preferable because a conjugated system is extended the most.

As the aryl group that mainly affects color purity, an aryl group substituted with an electron-donating group is preferred. Examples of the electron-donating group include alkyl groups and alkoxy groups. Particularly, aryl groups substituted with alkyl groups having 1 to 8 carbon atoms or alkoxy groups having 1 to 8 carbon atoms are preferable. Moreover, as an aryl group that mainly affects efficiency, an aryl group that has a bulky substituent, such as a tert-butyl group or an adamantyl group, is preferable.

From the viewpoint of heat resistance and color purity, it is preferable that $Ar^1$ and $Ar^4$ be aryl groups of the same structure and $Ar^2$ and $Ar^3$ be aryl group of the same structure.

Furthermore, from the viewpoint of dispersibility, it is more preferable that at least one of $Ar^1$ to $Ar^4$ be an unsubstituted phenyl group, an unsubstituted naphthyl group, or a phenyl or naphthyl group having at least one substituent selected from the group consisting of an alkyl group, an alkoxy group, and an aryl group. Especially, a phenyl or naphthyl group having at least one substituent selected from the group consisting of a methyl group, a methoxy group, a tert-butyl group, and a naphthyl group is particularly preferably mentioned.

From the viewpoint of luminance characteristics and heat resistance, $Ar^5$ is preferably an unsubstituted phenyl group, or a phenyl group having at least one substituent selected from the group consisting of an alkyl group, an alkoxy group, halogen, and a ring structure formed between adjacent substituents. Furthermore, from the viewpoint of heat resistance, $Ar^5$ is more preferably an unsubstituted phenyl group or a phenyl group having at least one substituent selected from the group consisting of a methyl group, a methoxy group, a tert-butyl group, fluorine, and a ring structure formed between adjacent substituents. In particular, it is preferable that at least one of the substituents be a methoxy group or fluorine because if so it becomes possible to achieve highly efficient light emission.

The aforementioned pyrromethene compound of formula (1) is not particularly limited and specific examples thereof include the following.

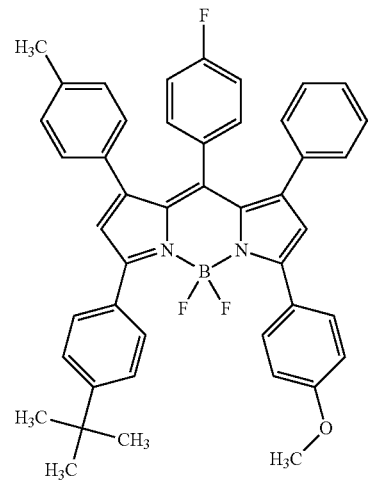

[1]

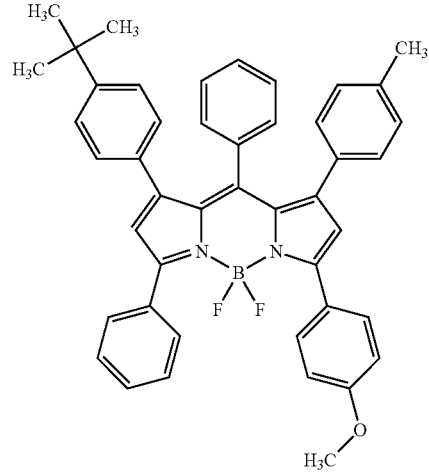

[2]

[3]
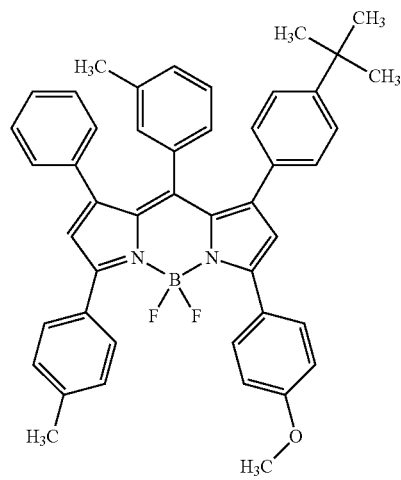
[4]
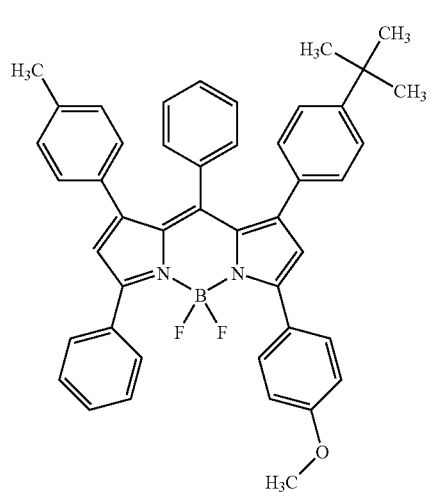
[5]
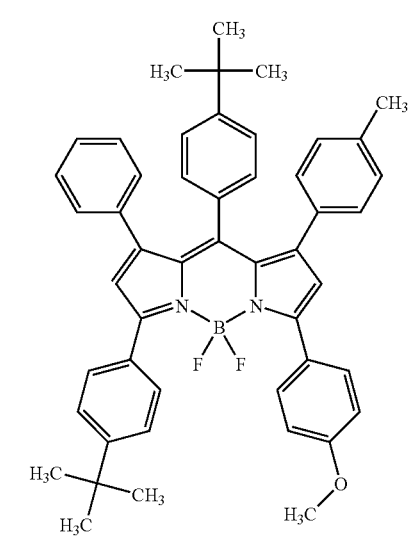
[6]
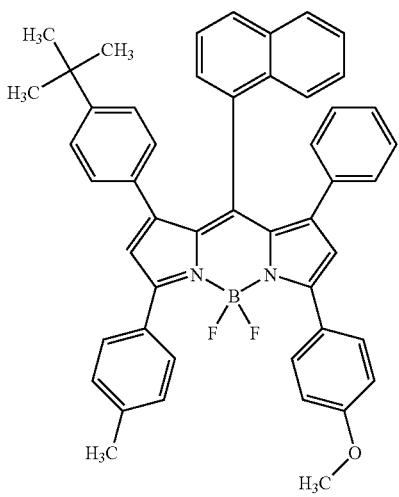
[7]
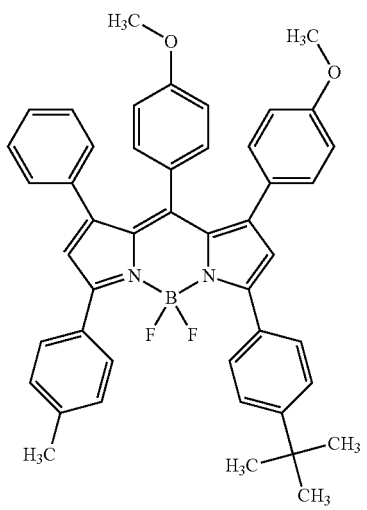
[8]
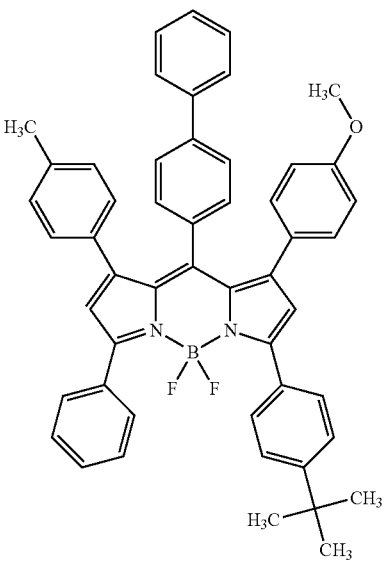

-continued
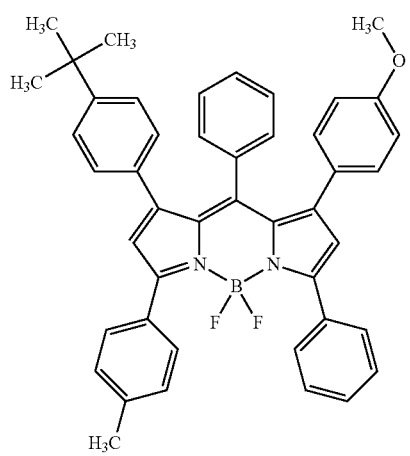
[9]
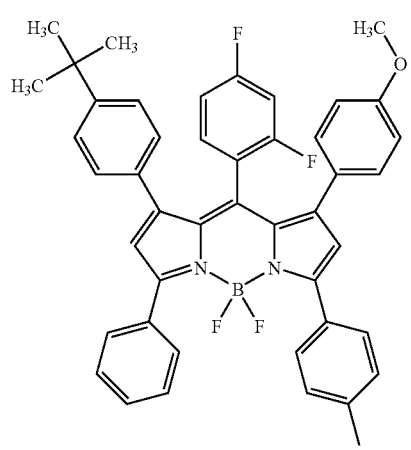
[10]
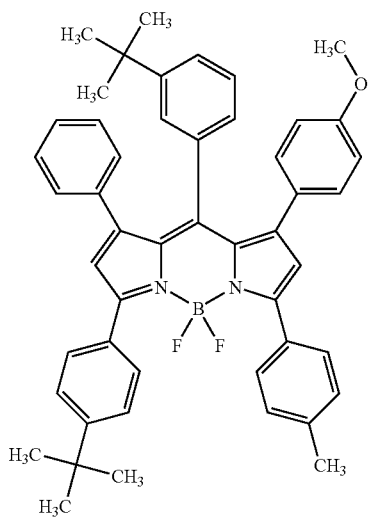
[11]
-continued
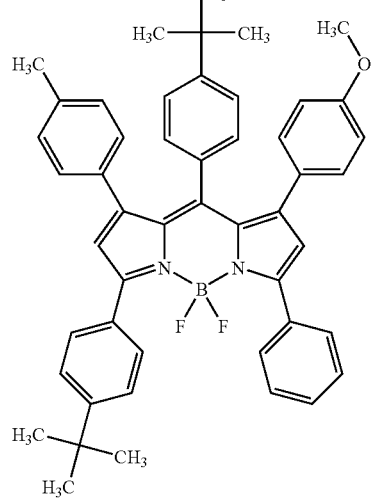
[12]
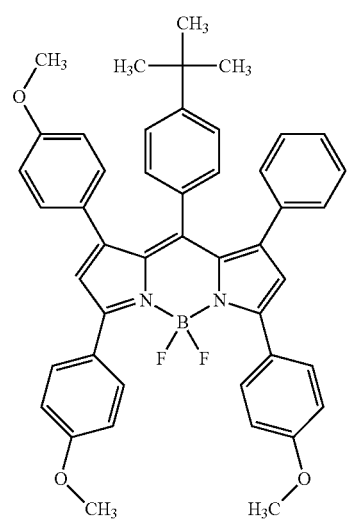
[13]
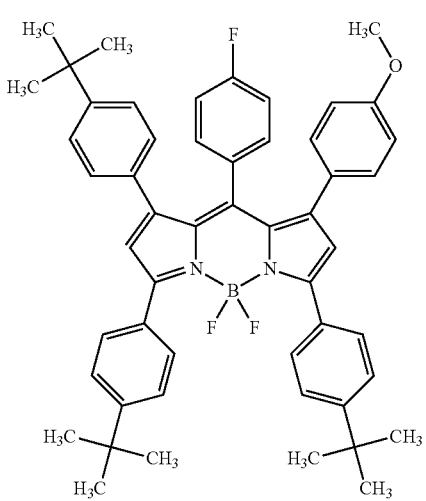
[14]

11
-continued
[15]
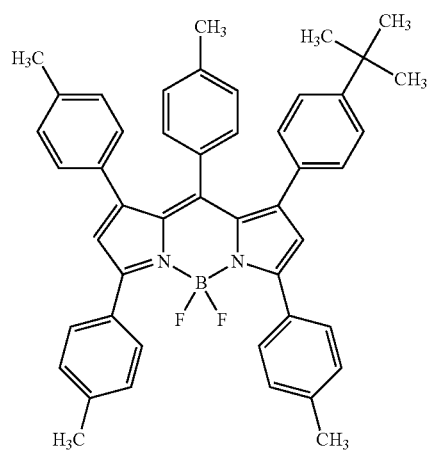
[16]
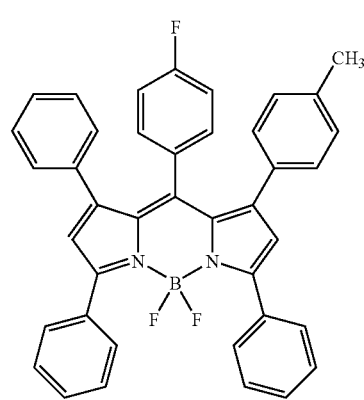
[17]
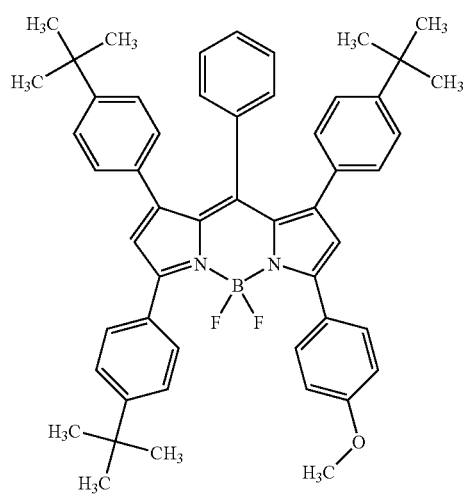
12
-continued
[18]
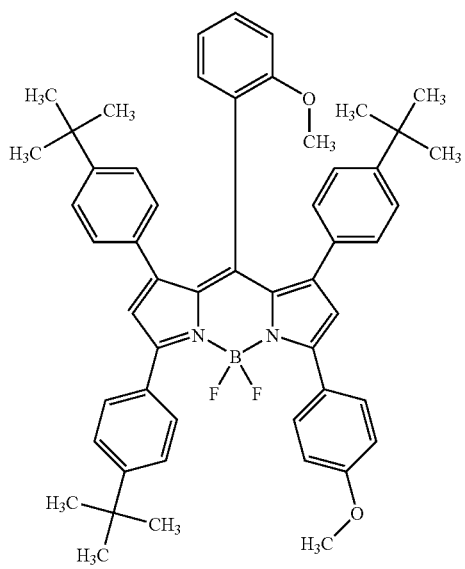
[19]
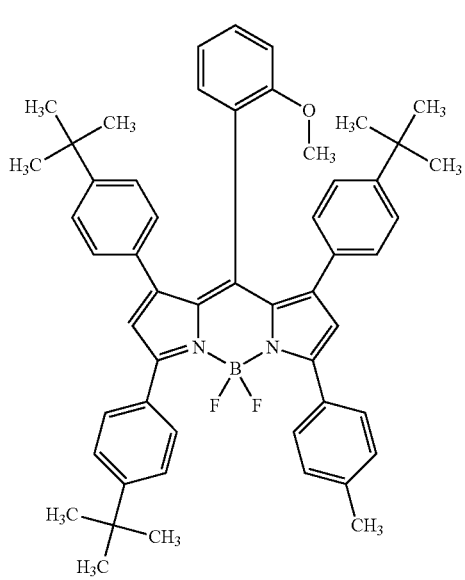
[20]
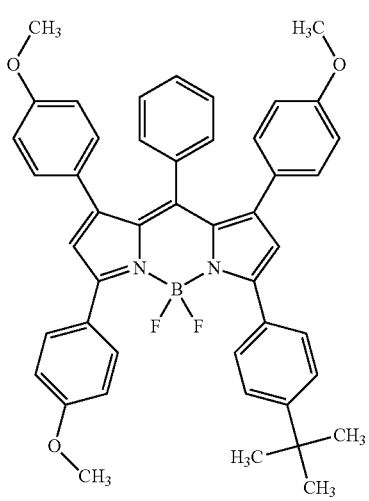

[21]
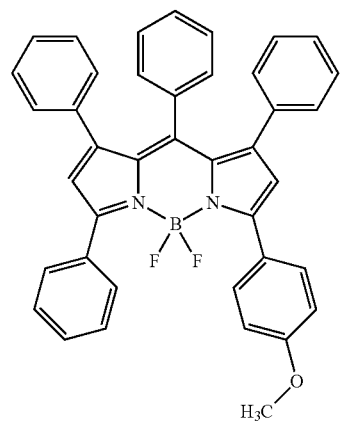
[22]
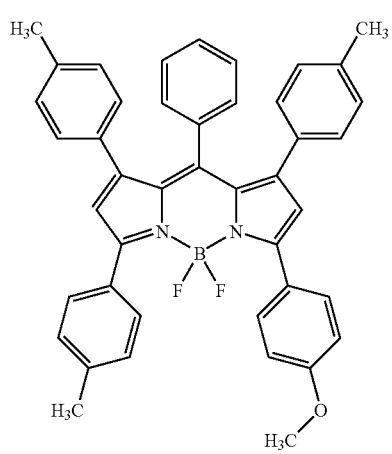
[23]
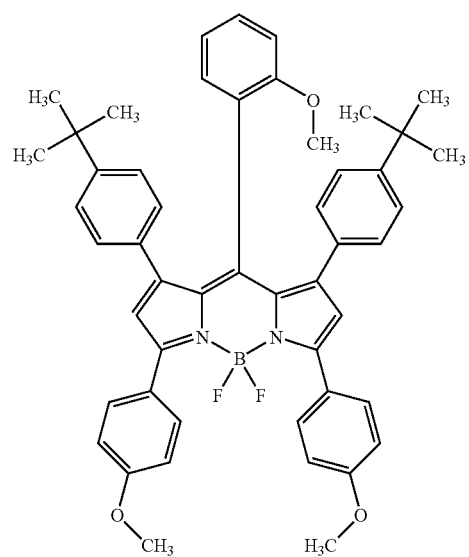
[24]
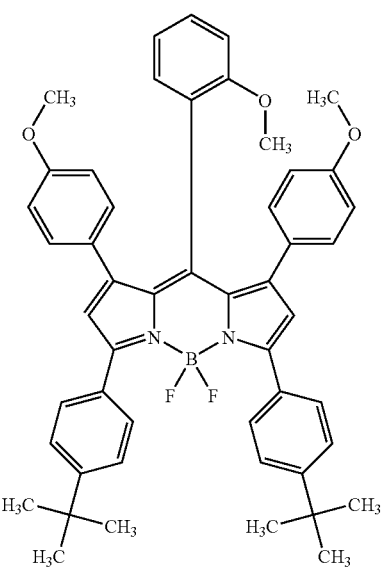
[25]
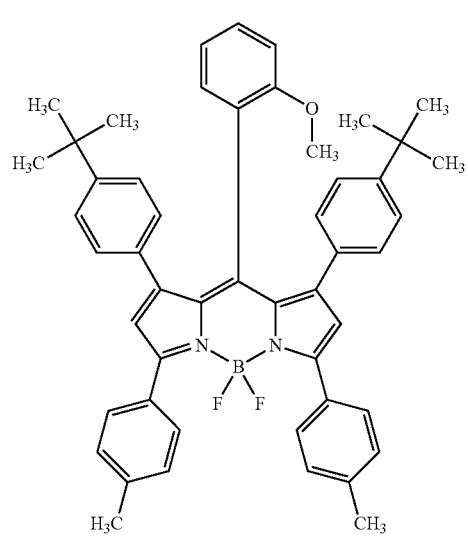
[26]
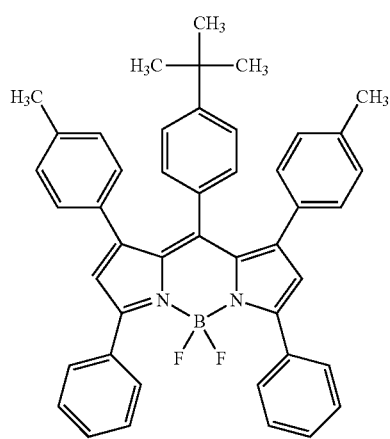

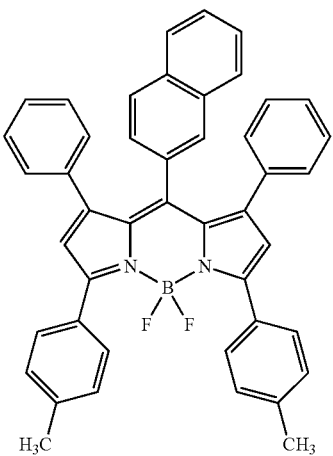
[27]
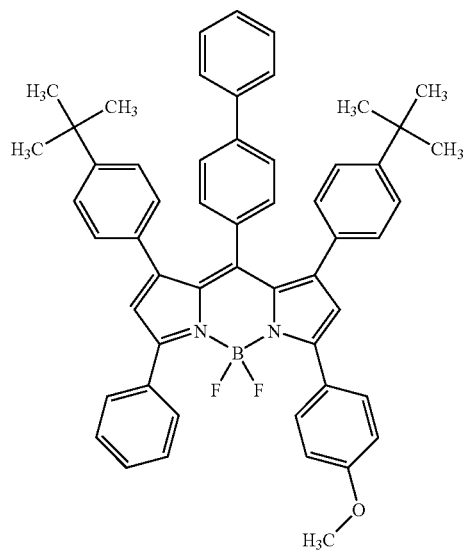
[28]
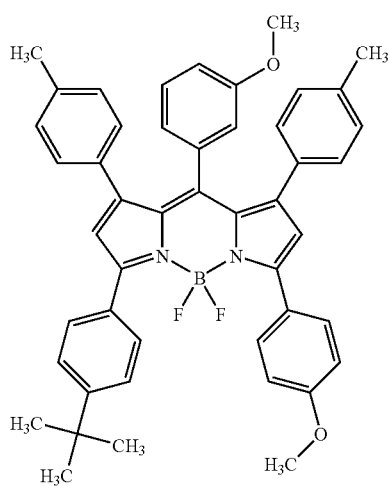
[29]
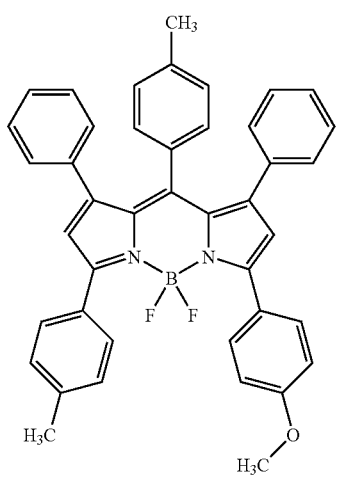
[30]
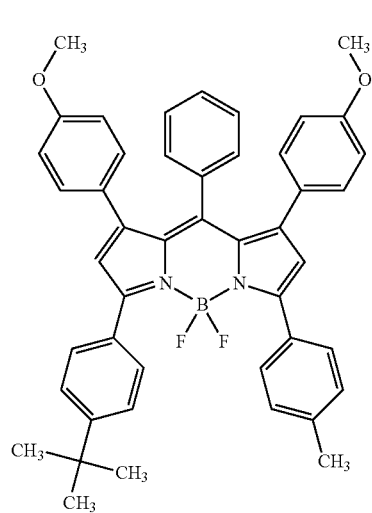
[31]
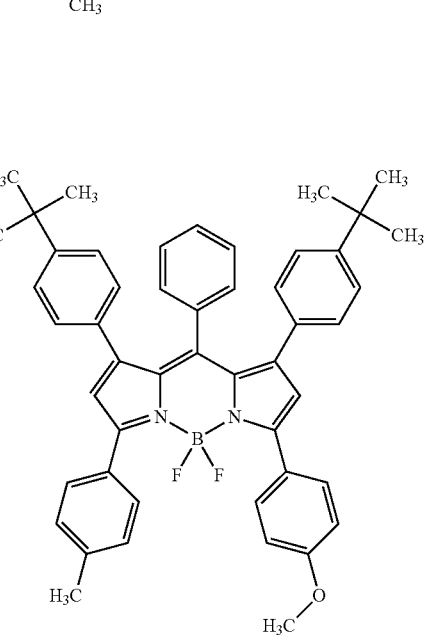
[32]

-continued
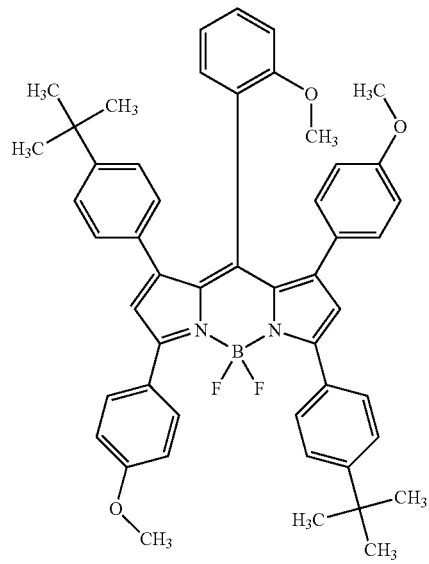
[33]
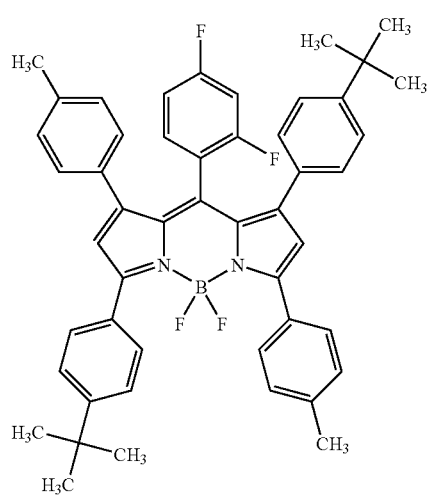
[34]
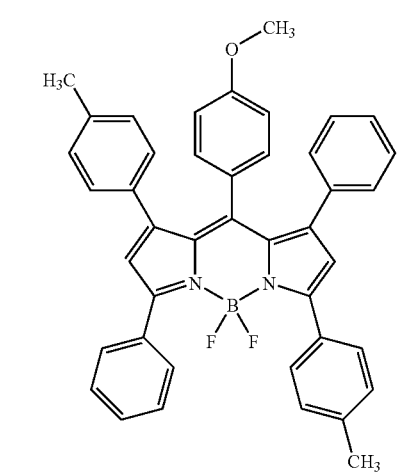
[35]
-continued
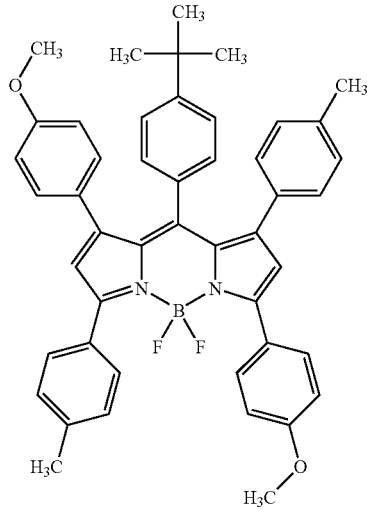
[36]
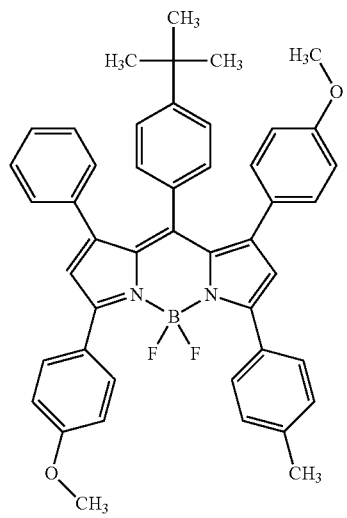
[37]
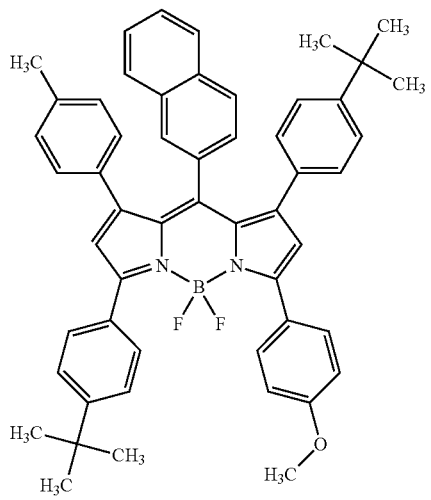
[38]

[39]
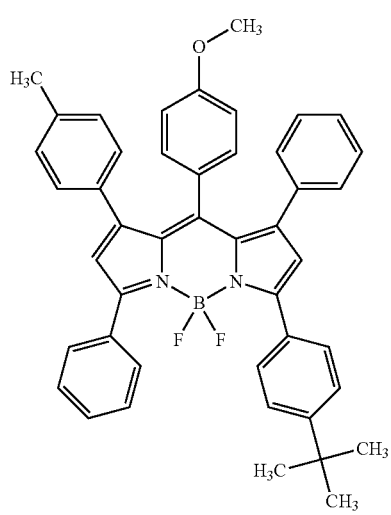
[40]
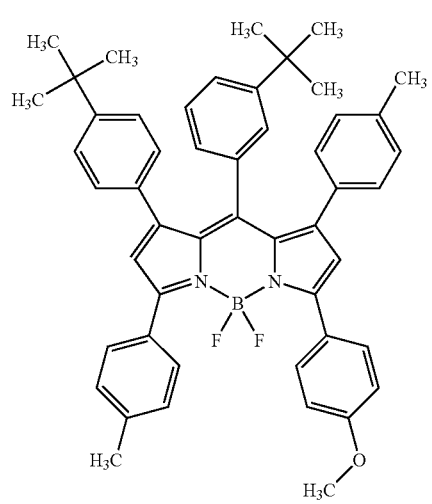
[41]
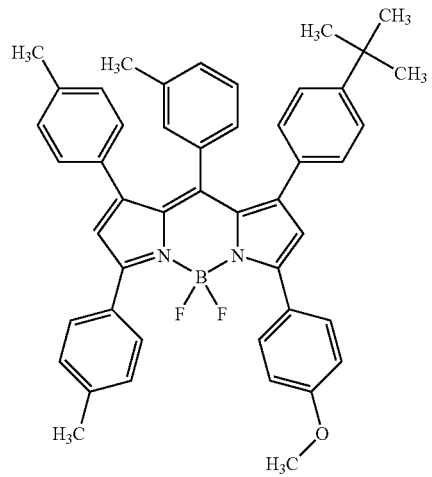
[42]
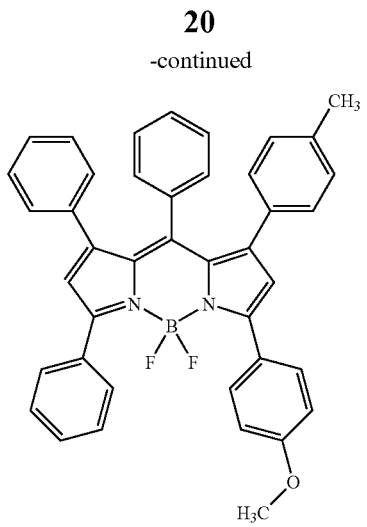
[43]
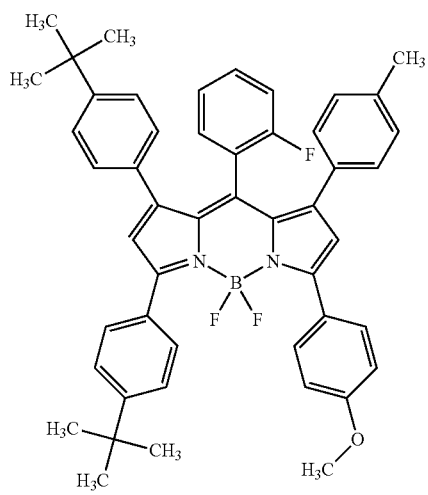
[44]
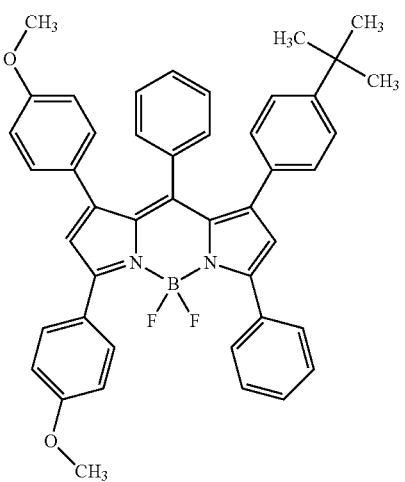

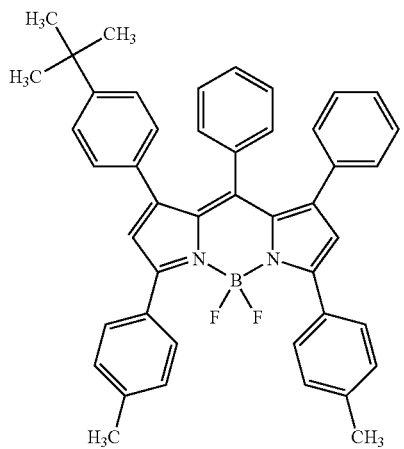
[45]
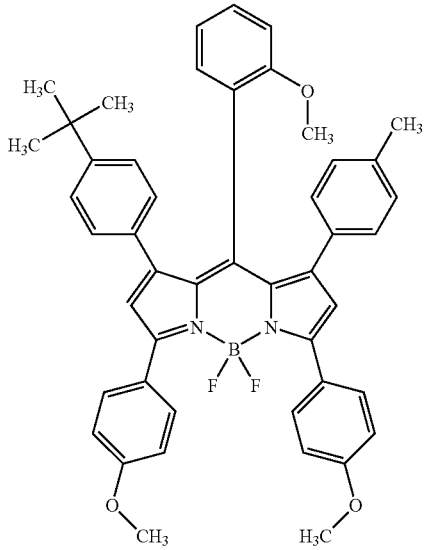
[48]
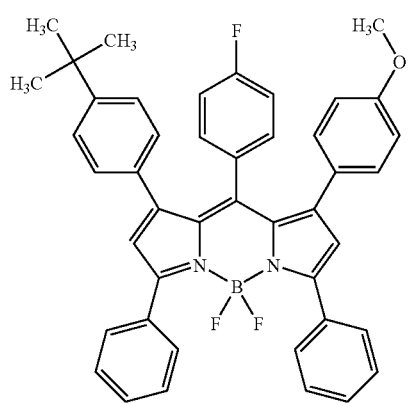
[46]
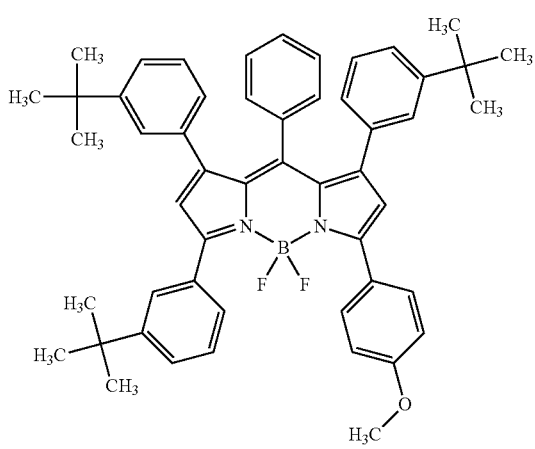
[49]
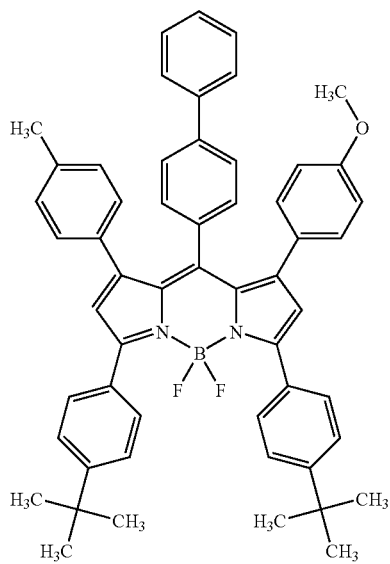
[47]
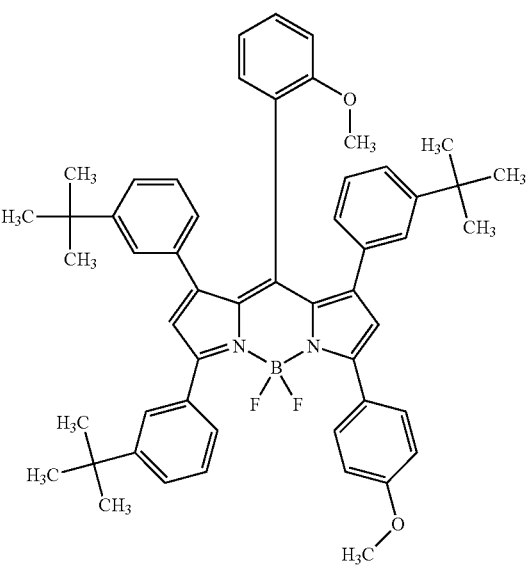
[50]

[51]
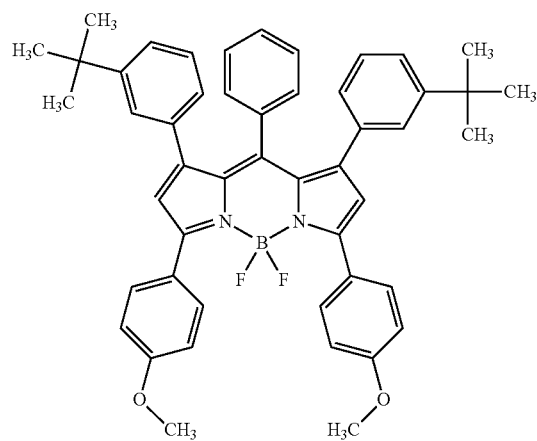

[52]
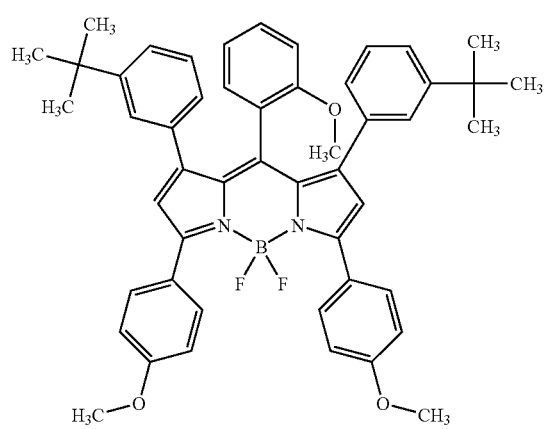

[53]
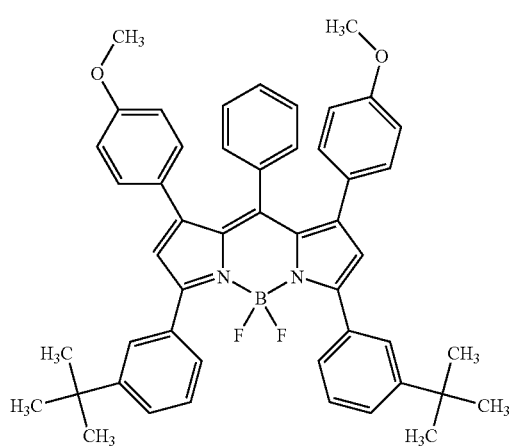

[54]
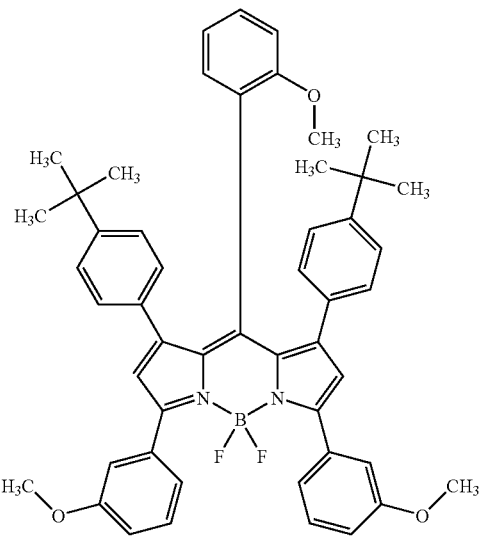

A known method can be used for the synthesis of the pyrromethene compound represented by the formula (1). For example, the compound of the formula (1) can be obtained by heating a compound represented by the following formula (2) and a compound represented by the following formula (3) in the presence of phosphorus oxychloride in 1,2-dichloroethane, and then reacting a compound represented by the following formula (4) in the presence of triethylamine in 1,2-dichloroethane. Here, $Ar^1$ to $Ar^5$, and $R^1$ to $R^4$ are the same as above. J represents halogen.

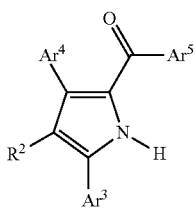

(2)

(3)

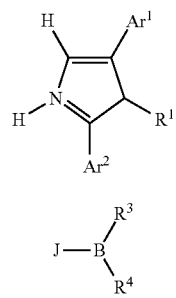

(4)

Embodiments of a light emitting device in the present invention will be described in detail below by way of examples. The light emitting device in an aspect of the present invention includes an anode, a cathode, and an organic layer existing between the anode and the cathode, and the organic layer includes at least an emissive layer and the emissive layer emits light by means of electric energy.

The organic layer may be of a structure composed only of an emissive layer, or has a layered structure of 1) hole transporting layer/emissive layer/electron transporting layer, 2)

emissive layer/electron transporting layer or 3) hole transporting layer/emissive layer. Each of the aforementioned layers may be composed of a single layer or two or more layers. When a hole transporting layer and an electron transporting layer are each composed of two or more layers, layers in contact with an electrode are sometimes referred to as a hole injection layer and an electron injection layer, respectively. In the following description, the hole injection material and the electron injection material are included in the hole transporting material and the electron transporting material, respectively.

In the light emitting device in an embodiment of the present invention, a light emitting device material containing the pyrromethene compound represented by the formula (1) is contained in the organic layer. The light emitting device material means a compound relating to light emission in a light emitting device and corresponds to either a material capable of emitting light itself or a material capable of assisting light emission. Specifically, the light emitting device material includes a hole transporting material, an emissive material, and an electron transporting material.

While the light emitting device material in an embodiment of the present invention may be used as a hole transporting material or an electron transporting material, it is suitably used as an emissive material because it has high light emitting performance. Although the light emitting device material in an embodiment of the present invention is suitably used as a red emissive material because it emits strong light in a red region, it can also be used as a material for a blue to green light emitting device and a white light emitting device. A white light emitting device can be obtained by laminating two or more materials different in color of emitted light. Specific examples thereof include a two-layer laminated system of a light-blue emissive material and an orange emissive material and a three-layer laminated system of a blue emissive material, a green emissive material, and a red emissive material. Since the light emitting device material in an embodiment of the present invention can be used suitably as a red emissive material, a white light emitting device can be obtained by forming a three-layer lamination structure with a blue emissive material, such as 4,4'-bis(2-(4-diphenylaminophenyl)ethenyl)biphenyl, and a green emissive material, such as 2,3,5,6-1H,4H-tetrahydro-9-(2'-benzothiazolyl)quinolidino[9,9a,1-gh]coumarin, as other emissive materials.

While the material of the anode is not particularly limited as long as it is a material capable of efficiently injecting holes into the organic layer, it is preferred to use a material having a comparatively large work function. Examples of the material of the anode include conductive metal oxides, such as tin oxide, indium oxide, zinc indium oxide and indium tin oxide (ITO); metals, such as gold, silver and chromium; inorganic conductive substances, such as copper iodide and copper sulfide; and conductive polymers, such as polythiophene, polypyrrole and polyaniline. These electrode materials may be used alone, or two or more materials may be laminated or mixed.

While the resistance of the anode is not particularly limited as long as a current required to perform light emission of the light emitting device can be supplied, a low resistance is preferred in view of power consumption of the light emitting device. For example, while the anode can function as an electrode when the resistance is 300 Ω/square or less, it is particularly preferred to use a product having a low resistance of 100 Ω/square or less because it has become possible to supply an ITO substrate having a resistance of about 10 Ω/square. The thickness of the anode can be optionally selected according to the resistance value, and it is usually from 100 to 300 nm.

In order to maintain the mechanical strength of a light emitting device, it is preferable to form the anode on a substrate. As the substrate, a substrate made of glass, such as soda glass or alkali-free glass, is suitably used. The thickness of the glass substrate may be a thickness enough for maintaining the mechanical strength and therefore a thickness of 0.5 mm or more is large enough. With regard to materials for glass, although alkali-free glass is preferred for the reason that less ion dissolution from glass is preferable, soda-lime glass on which a barrier coat of $SiO_2$ or the like has been applied, which is also commercially available, can also be used. In addition, if the anode functions stably, the substrate need not be glass; for example, the anode may be formed on a plastic substrate. The method of forming an anode is not particularly limited and, for example, an electron beam method, a sputtering method, and a chemical reaction method can be used.

The material to be used for a cathode is not particularly limited as long as it is a substance capable of efficiently injecting electrons into the organic layer, and examples thereof include platinum, gold, silver, copper, iron, tin, zinc, aluminum, indium, chromium, lithium, sodium, potassium, cesium, calcium and magnesium, or an alloy thereof. In order to improve device characteristics by improving electron injection efficiency, lithium, sodium, potassium, cesium, calcium, magnesium or an alloy containing such low work function metals is effective. However, since these low work function metals are often unstable in the atmospheric air, one of preferable examples is a method including doping the organic layer with a trace amount (1 nm or less in thickness measured with a thickness meter for vacuum deposition) of lithium or magnesium to obtain a highly stable electrode. An inorganic salt such as lithium fluoride can also be used. One preferable example of procedures to be used for electrode protection is to laminate a metal such as platinum, gold, silver, copper, iron, tin, aluminum or indium, an alloy using such metals, an inorganic substance such as silica, titania or silicon nitride, or an organic polymer compound such as polyvinyl alcohol, polyvinyl chloride or a hydrocarbon-based polymer compound. The method of forming a cathode is not particularly limited and, for example, resistance heating, electron beam, sputtering, ion plating and coating can be used.

The hole transporting layer is formed by a method of laminating or mixing one or two or more hole transporting materials or a method using a mixture of a hole transporting material and a polymer binder. A hole transporting layer may be formed by adding an inorganic salt such as iron(III) chloride to a hole transporting material. The hole transporting material is not particularly limited as long as it is a compound capable of forming a thin film, injecting holes from the anode and transporting holes. Preferable hole transporting materials include triphenylamine derivatives such as 4,4'-bis(N-(3-methylphenyl)-N-phenylamino)biphenyl, 4,4'-bis(N-(1-naphthyl)-N-phenylamino)biphenyl and 4,4',4"-tris(3-methylphenyl(phenyl)amino)triphenylamine; biscarbazole derivatives such as bis(N-allylcarbazole) and bis(N-alkylcarbazole); heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and polymers such as polycarbonate having the above monomer in the side chain, styrene derivatives, polythiophene, polyaniline, polyfluorene, polyvinylcarbazole, and polysilane.

The emissive layer may be made of either a mixture of a host material and a dopant material, or a host material alone. Each of the host material and the dopant material may be of a single kind or may be a combination of more than one kinds. The dopant material may be contained in the host material either entirely or partially. The dopant material may be either laminated with the host material or dispersed in the host material. The amount of the dopant material is preferably 10% by weight or less, and more preferably 2% by weight or less to the total amount of the host material and the dopant material because if it is too large, concentration quenching occurs. Regarding the doping method, the dopant material may be formed by a co-evaporation method with the host material, or evaporation may be performed after mixing the host material and the dopant material in advance. The pyrromethene compound in an embodiment of the present invention is used suitably as an emissive material. Although the compound may be used as a host material, it is used suitably as a dopant material because it is high in fluorescence quantum yield and has a small half band width of an emission spectrum.

As the dopant material, the pyrromethene compound represented by the formula (1) may be used singly, or more than one pyrromethene compounds may be used in combination. The pyrromethene compound represented by the formula (1) may also be mixed and used with one or more other dopant materials. As a dopant material which can be mixed, naphthalimide derivatives, such as bis(diisopropylphenyl)perylenetetracarboxylic imide, perynone derivatives, rare earth complexes containing acetylacetone or benzoylacetone and phenanthroline as a ligand, such as Eu complexes, 4-(dicyanomethylene)-2-methyl-6-(p-dimethylaminostyryl)-4H-pyran and analogues thereof, metal phthalocyanine derivatives, such as magnesium phthalocyanine and aluminum chlorophthalocyanine, rhodamine compounds, deazaflavin derivatives, coumarin derivatives, quinacridone derivatives, phenoxazine derivatives, oxazine derivatives, porphyrin-platinum complexes, and iridium complexes, such as a tris(2-phenylpyridyl)iridium complex and a tris{2-(2-thiophenyl)pyridyl}iridium complex, and so on may be allowed to be present, but the dopant material is not limited to these.

The host material to be contained in the light emitting material is not particularly limited, and there are preferably used fused ring derivatives, such as anthracene, naphthacene, and pyrene, metal-chelated oxynoid compounds including tris(8-quinolinolato)aluminum, bisstyryl derivatives, such as bisstyrylanthracene derivatives and distyrylbenzene derivatives, tetraphenylbutadiene derivatives, coumarin derivatives, oxadiazole derivatives, pyrrolopyridine derivatives, perynone derivatives, cyclopentadiene derivatives, oxadiazole derivatives, thiadiazolopyridine derivatives, pyrrolopyrrole derivatives, carbazole derivatives, such as 4,4'-bis(carbazolyl-N-yl)-4,4'-diphenyl and N,N'-diphenyl-3,3'-biscarbazole, triphenylamine compounds, such as N,N'-diphenyl-N,N'-di(3-methylphenyl)-4,4'-diphenyl-1,1'-diamine, indole derivatives, azole derivatives, such as triazole, oxadiazole, and imidazole, phenanthroline derivatives, quinoline derivatives, naphthyridine derivatives, oligopyridine derivatives, such as bipyridine and terpyridine, and polymers, such as polyphenylenevinylene derivatives, polyparaphenylene derivatives, and polythiophene derivatives. It is especially preferable to use a pyrene compound having an electron-donating substituent as a host material because the effect of improving efficiency and durability exerted upon combining the host material with the pyrromethene compound in an aspect of the present invention becomes remarkable. Moreover, it is preferable to use a naphthacene compound constituted only of aromatic hydrocarbons as a host material because the effect of improving efficiency and durability exerted upon combining the host material with the pyrromethene compound in an aspect of the present invention becomes remarkable.

In an embodiment of the present invention, the electron transporting layer is a layer that receives electrons injected from a cathode and further transports the electrons. The electron transporting layer preferably has high electron injection efficiency and efficiently transport injected electrons. Therefore, the electron transporting layer is preferably composed of a substance that has large electron affinity, high electron mobility and excellent stability and is less likely to generate, during production and use, impurities which will act as a trap. However, considering transportation balance between holes and electrons, if the electron transporting layer mainly plays a role of efficiently inhibiting holes from flowing toward the cathode from the anode without being recombined, there is exerted the same effect of improving luminance efficiency as that in the case where the electron transporting layer is made of a material having a high electron transportation capability even if the electron transporting layer is made of a material having not so high an electron transportation capability. Hence, a hole hindering layer capable of efficiently blocking a hole from moving is also included in the electron transporting layer in an aspect of the present invention as having the same meaning as the electron transporting layer.

Examples of the electron transporting material to be used for the electron transporting layer include fused polycyclic aromatic derivatives, such as naphthalene and anthracene, styryl-based aromatic ring derivatives typified by 4,4'-bis(diphenylethenyl)biphenyl, quinone derivatives, such as anthraquinone and diphenoquinone, phosphorus oxide derivatives, and various types of metal complexes, such as quinolinol complexes, e.g., tris(8-quinolinolate)aluminum (III), benzoquinolinol complexes, hydroxyazole complexes, azomethine complexes, tropolone metal complexes, and flavonol metal complexes. It is preferable to use a compound that is composed of one or more kinds of elements selected from the group consisting of carbon, hydrogen, nitrogen, oxygen, silicon, and phosphorus and has a heteroaryl ring structure containing electron-accepting nitrogen because the compound can reduce a driving voltage and highly efficient light emission can be obtained.

The electron-accepting nitrogen in the present invention means a nitrogen atom which forms a multiple bond with an adjacent atom thereof. Since the nitrogen atom has high electronegativity, the multiple bond has an electron-accepting property. Hence, a heteroaryl ring containing electron-accepting nitrogen has high electron affinity and is excellent in an electron transportation capability, and therefore it can reduce the driving voltage of a light emitting device by being used in the electron transporting layer. Examples of the heteroaryl ring containing electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzoxazole ring, a benzothiazole ring, a benzimidazole ring, and a phenanthroimidazole ring.

Examples of a preferred compound having a heteroaryl ring structure include benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, imidazopyridine derivatives, oligopyridine derivatives such as bipyridine and terpyridine, quinoxaline derivatives and naphthylidine derivatives. Among these compounds, there can be preferably used imidazole derivatives, such as 1-[4-(10-naphthalen-2-yl-anthracen-9-yl)phenyl]-2-phenyl-1H-benzimidazole; oxadiazole derivatives, such as 1,3-bis [(4-tert-butylphenyl)1,3,4-oxadiazolyl]phenylene; triazole derivatives, such as N-naphthyl-2,5-diphenyl-1,3,4-triazole; phenanthroline derivatives, such as bathocuproine and 1,3-bis(1,10-phenanthrolin-9-yl)benzene; benzoquinoline derivatives, such as 2,2'-bis(benzo[h]quinolin-2-yl)-9,9'-spirobifluorene; bipyridine derivatives, such as 2,5-bis(6'-(2', 2"-bipyridyl))-1,1-dimethyl-3,4-diphenylsilole; terpyridine derivatives, such as 1,3-bis(4'-(2,2':6'2"-terpyridinyl))benzene; and naphthylidine derivatives, such as bis(1-naphthyl)-4-(1,8-naphthylidin-2-yl)phenylphosphine oxide in view of the electron transportation capability.

While the aforementioned electron transporting materials may be used singly, two or more of the electron transporting materials may be mixed and used, or the electron transporting materials each may be mixed and used with one or more other electron transporting materials. Moreover, the electron transporting materials may also be mixed and used with alkali metals, inorganic salts containing alkali metals, complexes of alkali metals and organic substances, alkaline earth metals, inorganic salts containing alkaline earth metals, and complexes of alkaline earth metals and organic substances. While the ionization potential of the electron transporting layer is not particularly limited, it is preferably 5.5 eV or more and 8.0 eV or less, and more preferably 5.7 eV or more and 7.5 eV or less.

Examples of the method of forming each layer constituting the light emitting device include, but are not limited to, a resistance heating evaporation method, an electron beam evaporation method, a sputtering method, a molecular stacking method, a coating method, an ink-jet method, a printing method and a laser induced thermal transfer method. In view of device characteristics, a resistance heating evaporation method or an electron beam evaporation method is usually preferred.

Although the thickness of the organic layer depends on the resistance value of an emissive substance and cannot be limited, it is selected from between 1 nm and 1,000 nm. The thickness of each of the emissive layer, the electron transporting layer and the hole transporting layer is preferably 1 nm or more and 200 nm or less, and more preferably 5 nm or more and 100 nm or less.

The light emitting device in an embodiment of the present invention has a function of successfully converting electric energy into light. While a DC current is mainly used as the electric energy, a pulse current or an AC current can also be used. The values of the electric current and the voltage are not particularly limited. However, taking into consideration the power consumption and the life of the device, the values are preferably selected so that a maximum luminance can be obtained at an energy as low as possible.

The light emitting device in an embodiment of the present invention is used suitably as matrix and/or segment system displays.

In the matrix system, pixels for display are two-dimensionally disposed in lattice or mosaic, and characters and images are displayed by sets of pixels. The shape and size of the pixels are determined according to the intended application. In the case of image and character display by personal computers, monitors and televisions, there are normally used quadrangular pixels with up to 300 μm sides, and in the case of large-size displays such as display panels, there are normally used pixels with sides of the mm order. Pixels in the same color may be merely arrayed in the case of monochrome display, while pixels in red, green and blue are arrayed for indication in the case of color display. In a color display, the arrangement system typically includes a delta type system and a stripe type system. The method of driving the matrix may be either line-sequential driving or active matrix driving. While the line-sequential driving is simple in the structure of a light emitting device, active matrix driving is sometimes more advantageous when taking operation characteristics into consideration. The driving method is properly used according to the intended application.

The segment system is a system wherein a pattern is formed so as to display prescribed information and the range determined by the arrangement of the pattern is caused to emit light. Examples thereof include time and temperature displays in digital watches and thermometers, operation state displays in audio instruments and microwave cookers, and vehicle panel displays. The matrix display and the segment display may be present together in the same panel.

The light emitting device in an embodiment of the present invention can be employed suitably also as a backlight of various instruments. The backlight is mainly used for the purpose of improving visibility of a display device which itself emits no light, and it is used in liquid crystal display devices, watches, audio devices, automobile panels, display plates, and signs. The light emitting device of the present invention according to certain aspects is suitably used as the backlight of a liquid crystal display device, particularly a personal computer the thickness reduction of which is being studied. The light emitting device of the present invention can provide a backlight that is smaller in thickness and weight than conventional products.

EXAMPLES

The present invention will be described below with reference to examples, but the invention is not limited by these examples. The number of a compound in each of the following examples represents the number of a compound described in the aforementioned chemical formulae. Evaluation methods about structural analysis are described below.

$^1$H-NMR was measured in a chloroform-d solution by using superconductive FTNMR EX-270 (manufactured by JEOL Ltd.).

HPLC was measured by a 0.1 g/L chloroform solution using a high performance liquid chromatograph LC-10 (manufactured by Shimadzu Corporation). As the developing solvent of the column, a mixed solution of an aqueous 0.1% phosphoric acid solution and acetonitrile was used. Absorption spectra and fluorescence spectra were measured in a $4 \times 10^{-6}$ mol/L dichloromethane solution with a spectrophotometer U-3200 manufactured by Hitachi, Ltd. and a spectrofluorometer F-2500 manufactured by Hitachi, Ltd., respectively.

Synthesis Example 1

Method of Synthesizing Compound [17]

Under a nitrogen flow, 12.2 g of 4-tert-butylbenzaldehyde, 11.3 g of 4-methoxyacetophenone, and a mixed solution of 32 mL of 3 M aqueous potassium hydroxide solution and 20 mL of ethanol were stirred at room temperature for 12 hours. The precipitated solid was collected by filtration and washed twice with 50 mL of cold ethanol. After vacuum drying, 17 g of 3-(4-tert-butylphenyl)-1-(4-methoxyphenyl)propenone was obtained.

Next, a mixed solution of 17 g of 3-(4-tert-butylphenyl)-1-(4-methoxyphenyl)propenone, 21.2 g of diethylamine, 17.7 g of nitromethane, and 580 mL of methanol was refluxed by heating for 14 hours under a nitrogen flow. After cooling to room temperature, the solution was evaporated. Through purification by silica gel column chromatography and subsequent vacuum drying, 16 g of 3-(4-tert-butylphenyl)-1-(4-methoxyphenyl)-4-nitrobutan-1-one was obtained.

Next, a mixed solution of 230 mL of methanol and 46 mL of concentrated sulfuric acid was stirred at 0° C. under a nitrogen flow. A product prepared by adding 1.12 g of a potassium hydroxide powder to a mixed solution of 1.42 g of 3-(4-tert-butylphenyl)-1-(4-methoxyphenyl)-4-nitrobutan-1-one prepared in advance, 40 mL of methanol and 80 mL of tetrahydrofuran and stirring them at room temperature for 1 hour under a nitrogen flow was dropped slowly, followed by stirring at room temperature for another 1 hour. After cooling to 0° C., 50 mL of water was added, followed by neutralization with a 4 M aqueous sodium hydroxide solution and subsequent extraction with 50 mL of dichloromethane. The organic layer was washed twice with 30 mL of water, dried over sodium sulfate, and then evaporated to obtain a viscous material.

Next, a mixed solution of the obtained viscous material, 1.54 g of ammonium acetate and 20 mL of acetic acid was refluxed by heating at 100° C. for 1 hour under a nitrogen flow. After cooling to room temperature, ice water was added, followed by neutralization with a 4 M aqueous sodium hydroxide solution and subsequent extraction with 50 mL of dichloromethane. The organic layer was washed twice with 30 mL of water, dried over sodium sulfate, and then evaporated. After washing with 20 mL of ethanol and vacuum drying, 555 mg of 4-(4-tert-butylphenyl)-2-(4-methoxyphenyl)pyrrole was obtained.

Next, a mixed solution of 357 mg of 2-benzoyl-3,5-bis(4-tert-butylphenyl)pyrrole, 250 mg of 4-(4-tert-butylphenyl)-2-(4-methoxyphenyl)pyrrole, 138 mg of phosphorus oxychloride and 10 mL of 1,2-dichloroethane was refluxed by heating for 9 hours under a nitrogen flow. After cooling to room temperature, 847 mg of diisopropylethylamine and 931 mg of a boron trifluoride diethylether complex were added, and the mixture was stirred for 3 hours. To the mixture was poured 20 mL of water, followed by extraction with 30 mL of dichloromethane. The organic layer was washed twice with 20 mL of water, dried over magnesium sulfate, and then evaporated. Through purification by silica gel column chromatography and subsequent vacuum drying, 0.40 g of a reddish violet powder was obtained. The $^1$H-NMR analytical result of the resultant powder is as follows and confirmed that the reddish violet powder obtained above was the compound [17].

$^1$H-NMR (CDCl$_3$ (δ=ppm)): 1.18 (s, 18H), 1.35 (s, 9H), 3.85 (s, 3H), 6.37-6.99 (m, 17H), 7.45 (d, 2H), 7.87 (d, 4H).

This compound [17] was subjected to sublimation purification under a pressure of $1\times10^{-3}$ Pa at about 270° C. using an oil diffusion pump, and then used as a light emitting device material. The HPLC purity (area % at a measuring wavelength of 254 nm) was 99.7% before the sublimation purification and was 99.7% after the sublimation purification. Furthermore, the compound [17] exhibited the following photophysical properties.

Absorption spectrum: λmax 574 nm (solvent: dichloromethane)
Fluorescence spectrum: λmax 621 nm (solvent: dichloromethane)

Synthesis Example 2

Method of Synthesizing Compound [18]

Synthesis was performed in the same manner as in Synthesis Example 1 except for using 381 mg of 2-(2-methoxybenzoyl)-3,5-bis(4-tert-butylphenyl)pyrrole instead of 2-benzoyl-3,5-bis(4-tert-butylphenyl)pyrrole, so that 0.25 g of a reddish violet powder was obtained. The $^1$H-NMR analytical result of the resultant powder is as follows and confirmed that the reddish violet powder obtained above was the compound [18].

$^1$H-NMR (CDCl$_3$ (δ=ppm)): 1.19 (s, 18H), 1.35 (s, 9H), 3.42 (s, 3H), 3.85 (s, 3H), 5.72 (d, 1H), 6.20 (t, 1H), 6.43-6.99 (m, 14H), 7.43 (d, 2H), 7.88 (d, 4H).

This compound [18] was subjected to sublimation purification under a pressure of $1\times10^{-3}$ Pa at about 260° C. using an oil diffusion pump, and then used as a light emitting device material. The HPLC purity (area % at a measuring wavelength of 254 nm) was 99.5% before the sublimation purification and was 99.5% after the sublimation purification. Furthermore, the compound [18] exhibited the following photophysical properties.

Absorption spectrum: λmax 576 nm (solvent: dichloromethane)
Fluorescence spectrum: λmax 624 nm (solvent: dichloromethane)

Synthesis Example 3

Method of synthesizing compound [23]

A mixed solution of 300 mg of 4-(4-tert-butylphenyl)-2-(4-methoxyphenyl)pyrrole, 201 mg of 2-methoxybenzoyl-chloride, and 10 mL of toluene was heated at 120° C. for 6 hours under a nitrogen flow. After cooling to room temperature, evaporation was performed. After washing with 20 mL of ethanol and vacuum drying, 260 mg of 2-(2-methoxybenzoyl)-3-(4-tert-butylphenyl)-5-(4-methoxyphenyl)pyrrole was obtained.

Next, a mixed solution of 260 mg of 2-(2-methoxybenzoyl)-3-(4-tert-butylphenyl)-5-(4-methoxyphenyl)pyrrole, 180 mg of 4-(4-tert-butylphenyl)-2-(4-methoxyphenyl)pyrrole, 206 mg of methanesulfonic anhydride, and 10 mL of degassed toluene was heated at 125° C. for 7 hours under a nitrogen flow. After cooling to room temperature, 20 mL of water was poured, followed by extraction with 30 mL of dichloromethane. The organic layer was washed twice with 20 mL of water, followed by evaporation and vacuum drying.

Next, to a mixed solution of the obtained pyrromethene body and 10 mL of toluene were added 305 mg of diisopropylethylamine and 670 mg of a boron trifluoride diethylether complex, followed by stirring at room temperature for 3 hours. To the mixture was poured 20 mL of water, followed by extraction with 30 mL of dichloromethane. The organic layer was washed with 20 mL of water, dried over magnesium sulfate, and then evaporated. Through purification by silica gel column chromatography and subsequent vacuum drying, 0.27 g of a reddish violet powder was obtained. The $^1$H-NMR analytical result of the resultant powder is as follows and confirmed that the reddish violet powder obtained above was the compound [23].

$^1$H-NMR (CDCl$_3$ (δ=ppm)): 1.19 (s, 18H), 3.42 (s, 3H), 3.85 (s, 6H), 5.72 (d, 1H), 6.20 (t, 1H), 6.42-6.97 (m, 16H), 7.89 (d, 4H).

This compound [23] was subjected to sublimation purification under a pressure of $1\times10^{-3}$ Pa at about 270° C. using an oil diffusion pump, and then used as a light emitting device material. The HPLC purity (area % at a measuring wavelength of 254 nm) was 99.9% before the sublimation purification and was 99.9% after the sublimation purification. Furthermore, the compound [23] exhibited the following photophysical properties.
Absorption spectrum: λmax 583 nm (solvent: dichloromethane)
Fluorescence spectrum: λmax 630 nm (solvent: dichloromethane)

Example 1

A glass substrate (manufactured by ASAHI GLASS CO., LTD., 15 Ω/square, an electron beam deposition product) on which an ITO transparent conductive film had been accumulated in a thickness of 125 nm was cut to a size of 30 mm×40 mm, which ITO conductive film was patterned by a photolithographic method to produce a light emitting part and an electrode extraction part. The obtained substrate was subjected to ultrasonic cleaning with acetone and "SEMICOCLEAN 56" (manufactured by Furuuchi Chemical Corporation) for 15 minutes, and then washed with ultrapure water. Subsequently, the substrate was subjected to ultrasonic cleaning with isopropyl alcohol for 15 minutes, and then immersed in hot methanol for 15 minutes and dried. Immediately before the production of a device, this substrate was subjected to a UV-ozone treatment for 1 hour and further placed in a vacuum evaporation device, and then the device was evacuated until the degree of vacuum in the device reached $5 \times 10^{-5}$ Pa or less. First, by a resistance heating method, copper phthalocyanine was deposited in a thickness of 10 nm as a hole injecting material and 4,4'-bis(N-(1-naphthyl)-N-phenylamino)biphenyl was deposited in a thickness of 50 nm as a hole transporting material. Next, with regard to an emissive material, H-1 represented by the following formula was deposited as a host material and the compound [23] was deposited as a dopant material in a thickness of 40 nm so that the doping concentration would become 0.5%. Next, E-1 represented by the following formula was laminated in a thickness of 35 nm as an electron transporting material. Lithium fluoride was deposited in a thickness of 0.5 nm on the organic layer formed above, and then aluminum was deposited in a thickness of 1000 nm to form a cathode, whereby a device of 5 mm×5 mm square was produced. The film thickness as referred to herein is a value displayed by a quartz crystal oscillator type film thickness monitor. In the light emission spectrum produced when this light emitting device was subjected to a direct current drive of 40 mA/cm², high efficiency, high color purity red light emission with a peak wavelength of 634 nm and a luminance efficiency of 6.5 cd/A was obtained.

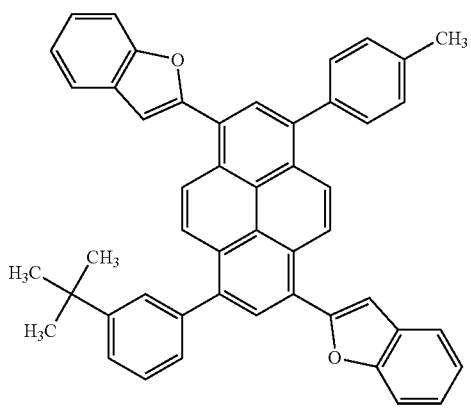

(H-1)

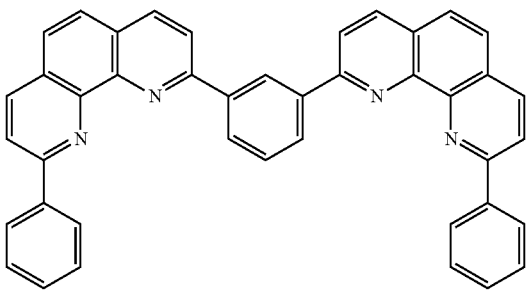

(E-1)

Comparative Example 1

A light emitting device was produced in the same manner as in Example 1 except for using D-1 shown below as a dopant material. In the light emission spectrum produced when this light emitting device was subjected to a direct current drive of 40 mA/cm², a high color purity, low efficiency red light emission with a peak wavelength of 629 nm and a luminance efficiency of 3.6 cd/A was obtained.

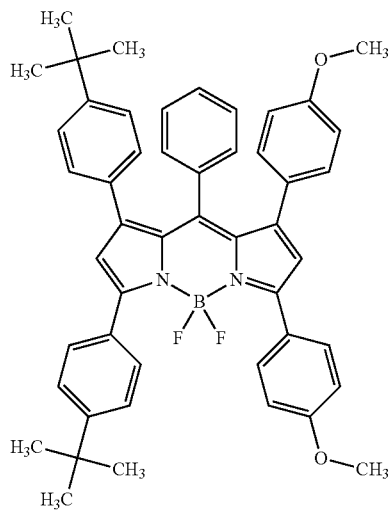

(D-1)

Comparative Example 2

A light emitting device was produced in the same manner as in Example 1 except for using D-2 shown below as a dopant material. In the light emission spectrum produced when this light emitting device was subjected to a direct current drive of 40 mA/cm², a low color purity, low efficiency red light emission with a peak wavelength of 611 nm and a luminance efficiency of 3.1 cd/A was obtained.

(D-2)

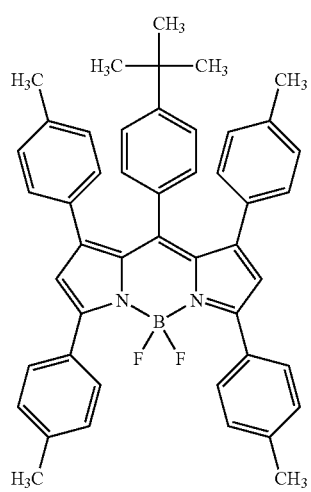

Examples 2 to 5

Light emitting devices were produced in the same manner as in Example 1 except for using materials shown in Table 1 as a host material, a dopant material, and an electron transporting material. The evaluation results of the respective examples are provided in Table 1. In Table 1, H-2 and H-3 are the host materials represented by the following formulae, respectively.

(H-2)

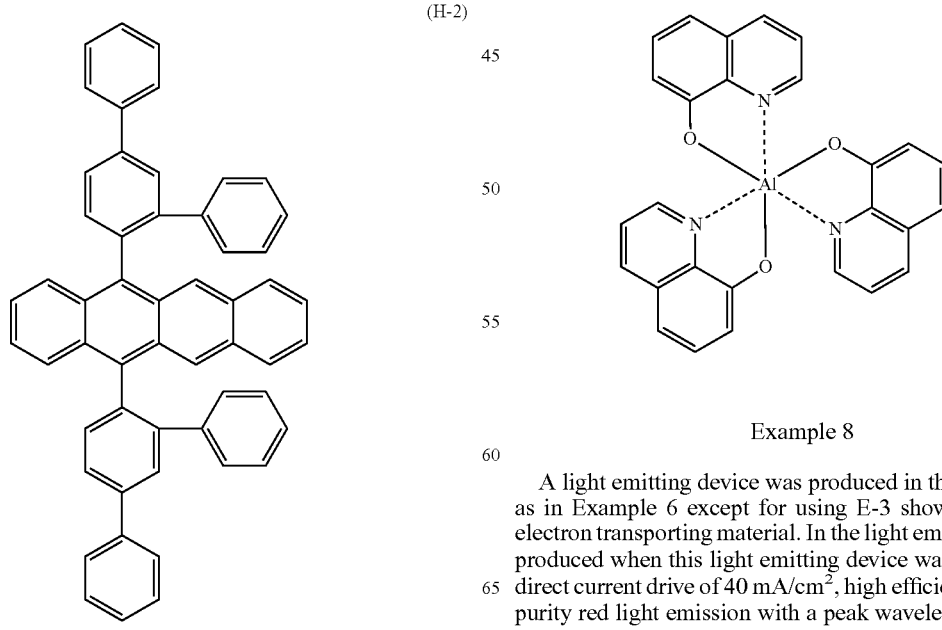

-continued (H-3)

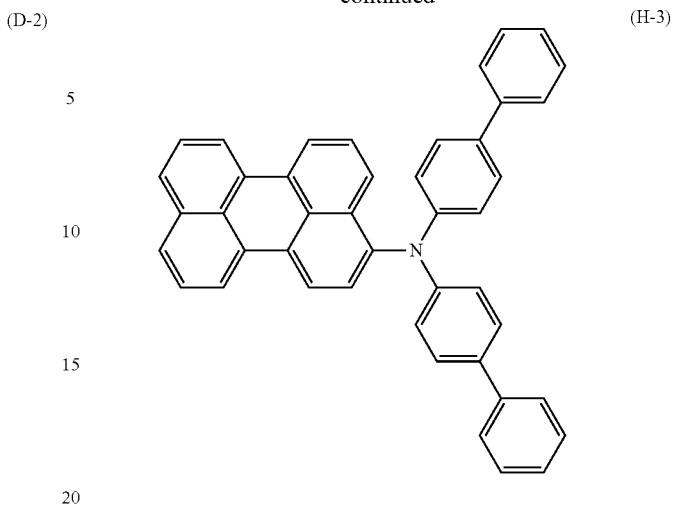

Example 6

A light emitting device was produced in the same manner as in Example 1 except for changing the thickness of the emissive layer to 60 nm and the thickness of the electron transporting layer to 15 nm. In the light emission spectrum produced when this light emitting device was subjected to a direct current drive of 40 mA/cm$^2$, high efficiency, high color purity red light emission with a peak wavelength of 634 nm and a luminance efficiency of 4.3 cd/A was obtained.

Example 7

A light emitting device was produced in the same manner as in Example 6 except for using E-2 shown below as an electron transporting material. In the light emission spectrum produced when this light emitting device was subjected to a direct current drive of 40 mA/cm$^2$, high efficiency, high color purity red light emission with a peak wavelength of 634 nm and a luminance efficiency of 4.0 cd/A was obtained.

(E-2)

Example 8

A light emitting device was produced in the same manner as in Example 6 except for using E-3 shown below as an electron transporting material. In the light emission spectrum produced when this light emitting device was subjected to a direct current drive of 40 mA/cm$^2$, high efficiency, high color purity red light emission with a peak wavelength of 633 nm and a luminance efficiency of 4.2 cd/A was obtained.

TABLE 1

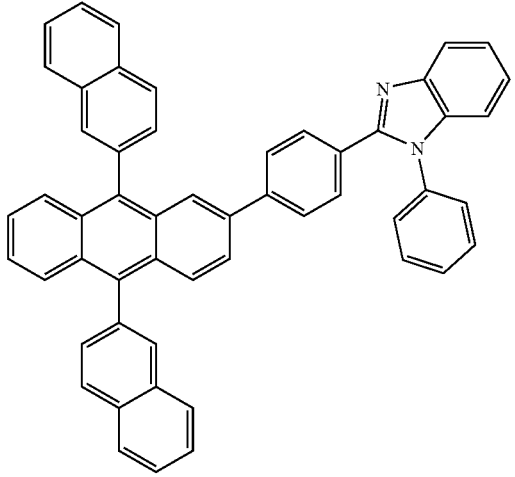 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

(E-3)

| | Emissive Layer | | Electron | Colar of | Peak Wave- | Luminance |
|---|---|---|---|---|---|---|
| | Host Material | Dopant Material | Transporting Material | Light Emission | length (nm) | Efficiency (cd/A) |
| Example 1 | H-1 | Compound [23] | E-1 | Deep Red | 634 | 6.5 |
| Comparative Example 1 | H-1 | D-1 | E-1 | Deep Red | 629 | 3.6 |
| Comparative Example 2 | H-1 | D-2 | E-1 | Red | 611 | 3.1 |
| Example 2 | H-1 | Compound [17] | E-1 | Deep Red | 626 | 5.7 |
| Example 3 | H-1 | Compound [18] | E-1 | Deep Red | 627 | 5.4 |
| Example 4 | H-2 | Compound [23] | E-1 | Deep Red | 634 | 6.2 |
| Example 5 | H-3 | Compound [23] | E-1 | Deep Red | 633 | 4.4 |
| Example 6 | H-1 | Compound [23] | E-1 | Deep Red | 634 | 4.3 |
| Example 7 | H-1 | Compound [23] | E-2 | Deep Red | 634 | 4.0 |
| Example 8 | H-1 | Compound [23] | E-3 | Deep Red | 633 | 4.2 |

Example 9

A glass substrate (manufactured by ASAHI GLASS CO., LTD., 15 Ω/square, an electron beam deposition product) on which an ITO transparent conductive film was accumulated in a thickness of 150 nm was cut to a size of 30 mm×40 mm, which ITO conductive film was patterned into a stripe of 300 μm-pitch (a residual width of 270 μm)×32 pieces by a photolithographic method. One side of the ITO stripe in a long side direction was widened to 1.27 mm-pitch (an opening width of 800 μm) in order to facilitate electrical connection to the exterior. The obtained substrate was subjected to ultrasonic cleaning with acetone and "SEMICOCLEAN 56" (commercial name, manufactured by Furuuchi Chemical Corporation) each for 15 minutes and then washed with ultrapure water. Subsequently, the substrate was subjected to ultrasonic cleaning with isopropyl alcohol for 15 minutes, and then immersed in hot methanol for 15 minutes and dried. Immediately before production of the device, this substrate was subjected to a UV-ozone treatment for 1 hour and placed in a vacuum evaporation device, and then the device was evacuated until the degree of vacuum in the device reached $5 \times 10^{-4}$ Pa or less. First, by a resistance heating method, 4,4'-bis(N-(1-naphthyl)-N-phenylamino)biphenyl was deposited in a thickness of 150 nm as a hole transporting material. Next, H-1 was deposited as a host material and the compound [23] was deposited as a dopant material in a thickness of 40 nm so that the doping concentration would become 0.5%. Next, E-1 was laminated in a thickness of 35 nm as an electron transporting material. The film thickness as referred to herein is a value displayed by a quartz crystal oscillator type film thickness monitor. Next, a mask such that 16 pieces of 250 μm-openings (corresponding to a residual width of 50 μm and 300 μm-pitch) were made on a Kovar plate with a thickness of 50 μm by wet etching was subjected to mask exchange so as to be orthogonal to the ITO stripe in a vacuum and fixed with a magnet from the back surface so that the mask and the ITO substrate might adhered closely. After deposition of lithium fluoride in 0.5 nm, aluminum was deposited in 200 nm to produce a 32×16 dot matrix device. When the device was subjected to matrix drive, characters were indicated successfully without crosstalk.

The light emitting device material in embodiments of the present invention can provide a light emitting device material that can be used for a light emitting device, and so on, and is useful as a fluorescent dye. According to an aspect of the present invention, a light emitting device having high luminance efficiency and an excellent color purity can be obtained. The light emitting device in an embodiment of the present invention can be used for display elements, flat panel displays, backlights, lighting, interiors, signs, signboards, electronic cameras, light signal generators, and the like.

What is claimed is:

1. A light emitting device, wherein at least an emissive layer exists between an anode and a cathode and emits light by means of electric energy and at least an electron transporting layer exists between the emissive layer and the cathode, the emissive layer comprising a light emitting device material comprising at least one host material and at least one dopant material, wherein the at least one host material includes a member selected from the group consisting of compounds represented by formulae (H-1) and (H-2):

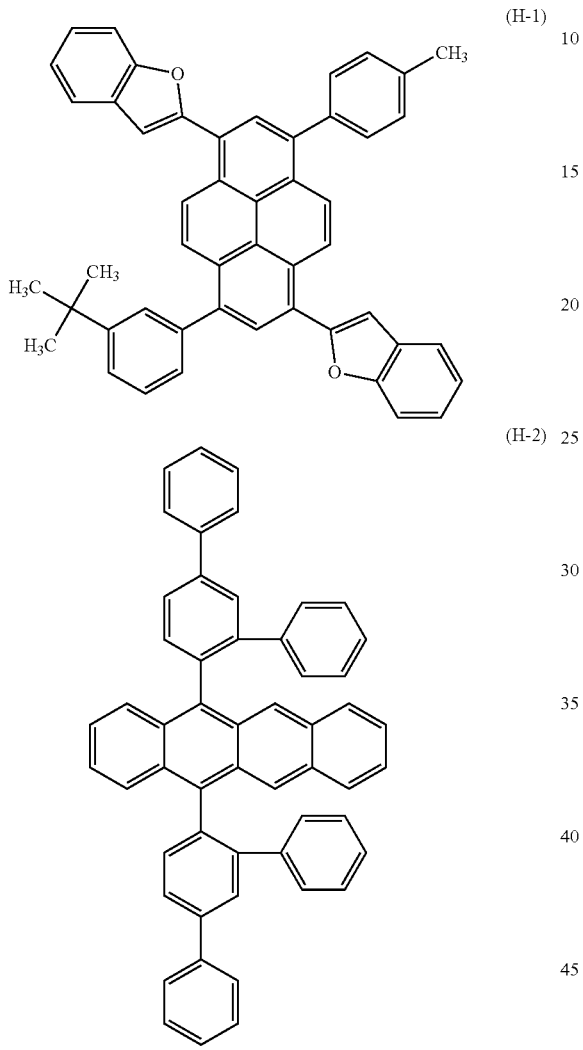

and the at least one dopant material includes a pyrromethene compound represented by the following formula (1):

[Formula 1]

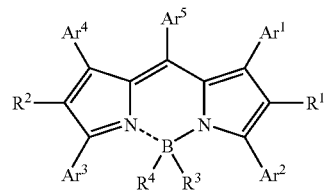

wherein $R^1$ to $R^4$ each may be the same or different and are selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an aryl thioether group, an aryl group, a heteroaryl group, a halogen, a cyano group, an amino group, a silyl group, and a ring structure formed between adjacent substituents, $Ar^1$ to $Ar^5$ each represent an aryl group, provided that $Ar^1 \ne Ar^2$ or $Ar^3 \ne Ar^4$, wherein $\ne$ means that the groups are different in structure and wherein at least one of $Ar^1$ to $Ar^4$ is an unsubstituted phenyl group, an unsubstituted naphthyl group, or a phenyl or naphthyl group having at least one substituent selected from the group consisting of a methyl group, a methoxy group, a tert-butyl group, and a naphthyl group; and wherein the electron transporting layer comprises a compound represented by formula (E-1):

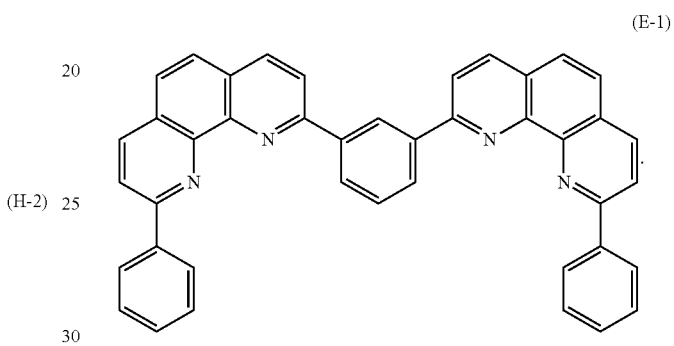

2. The light emitting device according to claim 1, wherein $Ar^5$ of the formula (1) is an unsubstituted phenyl group, or a phenyl group having at least one substituent selected from the group consisting of an alkyl group, an alkoxy group, a halogen, and a ring structure formed between adjacent substituents.

3. The light emitting device according to claim 1, wherein $Ar^2$ and $Ar^3$ in the formula (1) are the same or different and are phenyl groups substituted with an alkyl group or an alkoxy group.

4. The light emitting device according to claim 1, wherein both $R^3$ and $R^4$ are fluorine.

5. The light emitting device of claim 1, wherein each of $Ar^1$ to $Ar^4$ is a phenyl group having a substituent selected from the group consisting of a methoxy group and a tert-butyl group.

6. The light emitting device of claim 1, wherein $Ar^5$ is an unsubstituted phenyl group or a phenyl group substituted with a methoxy group.

7. The light emitting device of claim 1, wherein $R^1$ and $R^2$ are hydrogen.

8. The light emitting device of claim 1, wherein $R^3$ and $R^4$ are halogen.

9. The light emitting device of claim 1, wherein each of $Ar^1$ to $Ar^4$ is a phenyl group having a substituent selected from the group consisting of a methoxy group and a tert-butyl group, $Ar^5$ is an unsubstituted phenyl group or a phenyl group substituted with a methoxy group, $R^1$ and $R^2$ are hydrogen, and $R^3$ and $R^4$ are halogen.

10. The light emitting device of claim 1, wherein $R^1$ and $R^2$ are each hydrogen, $R^3$ and $R^4$ are each F, $Ar^1$ and $Ar^4$ are each a phenyl group substituted with a tert-butyl group, $Ar^2$ and $Ar^3$ are each a phenyl group substituted with a methoxy group, and $Ar^5$ is an unsubstituted phenyl group.

11. The light emitting device of claim 1, wherein $R^1$ and $R^2$ are each hydrogen, $R^3$ and $R^4$ are each F, $Ar^1$ and $Ar^4$ are each a phenyl group substituted with a tert-butyl group, $Ar^2$ is a phenyl group substituted with a methoxy group, $Ar^3$ is a phenyl group substituted with a tert-butyl group, and $Ar^5$ is an unsubstituted phenyl group.

12. The light emitting device of claim 1, wherein $R^1$ and $R^2$ are each hydrogen, $R^3$ and $R^4$ are each F, $Ar^1$ and $Ar^4$ are each a phenyl group substituted with a tert-butyl group, $Ar^2$ is a phenyl group substituted with a methoxy group, $Ar^3$ is a phenyl group substituted with a tert-butyl group, and $Ar^5$ is a phenyl group substituted with a methoxy group.

13. The light emitting device of claim 1, wherein $R^1$ and $R^2$ are each hydrogen, $R^3$ and $R^4$ are each F, $Ar^1$ and $Ar^4$ are each a phenyl group substituted with a tert-butyl group, $Ar^2$ and $Ar^3$ are each a phenyl group substituted with a methoxy group, and $Ar^5$ is a phenyl group substituted with a methoxy group.

* * * * *

UNITED STATES PATENT AND TRADEMARK OFFICE
CERTIFICATE OF CORRECTION

PATENT NO. : 8,962,155 B2
APPLICATION NO. : 12/740821
DATED : February 24, 2015
INVENTOR(S) : Kazumasa Nagao et al.

It is certified that error appears in the above-identified patent and that said Letters Patent is hereby corrected as shown below:

Title Page, item (56) References Cited, FOREIGN PATENT DOCUMENTS, duplicate reference "JP 200553900, 3/2005", should be deleted.

Title Page, item (57) ABSTRACT, "exellent" should read -- excellent --.

Signed and Sealed this
Thirtieth Day of June, 2015

Michelle K. Lee
*Director of the United States Patent and Trademark Office*